United States Patent [19]
Respess

[11] Patent Number: 5,599,662
[45] Date of Patent: Feb. 4, 1997

[54] OLICONUCLEOTIDE PRIMERS AND PROBES FOR THE DETECTION OF HIV-1

[75] Inventor: Richard A. Respess, Alameda, Calif.

[73] Assignee: Hoffmann-La Roche Inc., Nutley, N.J.

[21] Appl. No.: 390,192

[22] Filed: Feb. 17, 1995

[51] Int. Cl.$^6$ .......................... C07H 21/04; C12Q 1/70; C12P 19/34
[52] U.S. Cl. ................... 435/5; 435/6; 435/91.2; 536/24.32; 536/24.33; 935/8; 935/17; 935/78
[58] Field of Search .................... 435/6, 5, 91.2; 536/24.32, 24.33; 935/77, 78, 17, 18, 8

[56] References Cited

FOREIGN PATENT DOCUMENTS

| | | |
|---|---|---|
| 0345375 | 12/1989 | European Pat. Off. . |
| 0591914 | 4/1994 | European Pat. Off. . |
| 0617132 | 9/1994 | European Pat. Off. . |
| 9216180 | 10/1992 | WIPO . |
| 9313223 | 7/1993 | WIPO . |

OTHER PUBLICATIONS

Kwok et al., 1990, "Effects of Primer–Template Mismatches on the Polymerase Chain Reaction: Human Immunodeficiency Virus Type 1 Model Studies" Nucleic Acids Research 18(4):999–1005.

Coutlee et al., 1991, "The Polymerase Chain Reaction: A New Tool for the Understanding and Diagnosis of HIV–1 Infection at the Molecular Level" Molecular and Cellular Probes 5:241–259.

Jackson et al., 1991, "Non–Isotopic Polymerase Chain Reaction Methods for the Detection of HIV–1 in Ugandan Mothers and Infants" AIDS 5:1463–1467.

Chang et al., 1993, "Detection of Variability in Natural Populations of Viruses by Polymerase Chain Reaction" Methods in Enzymology 224:428–438.

Gurtler et al., Mar., 1994, "A New Subtype of Human Immunodeficiency Virus Type 1 (MVP–5180) from Cameroon" J. Virology 68(3):1581–1585.

Haesevelde et al., Mar., 1994, "Genomic Cloning and Complete Sequence Analysis of a Highly Divergent African Human Immunodeficiency Virus Isolate" J. Virology 68(3):1586–1596.

Loussert–Ajaka et al., Jun., 1994, "HIV–1/HIV–2 Seronegativity in HIV–1 Subtype O Infected Patients" Lancet 343:1393–1394.

Kwok et al., 1994, "A Guide to the Design and Use of Mismatched and Degenerate Primers" PCR Methods and Applications 3:S39–S47.

Fransen et al., 1994, "Design and Evaluation of New, Highly Sensitive and Specific Primers and Polymerase Reaction Detection of HIV–1 Infected Primary Lymphocytes" Molecular and Cellular Porbes 8:317–322.

*Primary Examiner*—Carla J. Myers
*Attorney, Agent, or Firm*—George W. Johnston; Stacey R. Sias; Douglas A. Petry

[57] ABSTRACT

The present invention provides improved primers for the polymerase chain reaction (PCR) amplification of a nucleic acid sequence from the pol gene of the human immunodeficiency virus type 1 (HIV-1). The invention also provides improved probes for the detection of the nucleic acid amplified using the primers of the invention. The primers and amplification methods of the invention enable the detection of HIV-1 from any of the known subtypes. The probes of the invention enable simple and rapid hybridization detection assays for detecting amplified HIV-1 nucleic acid.

12 Claims, No Drawings

OLIGONUCLEOTIDE PRIMERS AND PROBES FOR THE DETECTION OF HIV-1

BACKGROUND OF THE INVENTION

1. Field of the Invention

The present invention relates to the field of molecular biology and nucleic acid chemistry. More specifically, it relates to methods and reagents for detecting human immunodeficiency virus (HIV-1). The invention therefore has applications in the field of medicine generally, medical diagnostics specifically, and the field of molecular biology.

2. Description of Related Art

The invention of the polymerase chain reaction (PCR), a method for amplifying specific sequences of nucleic acids, makes possible the rapid detection of nucleic acids present in a sample in what was previously an undetectably low quantity (see U.S. Pat. Nos. 4,683,195; 4,683,202; and 4,965,188, each of which is incorporated herein by reference). A preferred method of detecting amplified nucleic acid is by hybridization with a sequence-specific oligonucleotide probe (see Saiki et al, 1986, *Nature* 324:163–166, incorporated herein by reference).

The use of PCR and probe hybridization to amplify and detect HIV-1 nucleic acid is reviewed in Kwok, 1992, *Ann. Med.* 24:211–214, and Coutlee et al., 1991, *Mol. Cell. Probes* 5:241–259, both incorporated herein by reference. PCR-based HIV-1 detection assays are described in, for example, U.S. Pat. Nos. 5,008,182 and 5,176,775, Kellogg and Kwok, 1990, in PCR Protocols: A Guide to Methods and Applications (ed. Innis et al., Academic Press, San Diego, Calif.):337–347, and Jackson et. al., 1991, *AIDS* 5:1463–1467, each incorporated herein by reference. In addition, reagents for the amplification and detection of HIV-1 are commercially available.

HIV-1 displays considerable genomic sequence variability not only between isolates from different individuals, but also between isolates from the same individual over time. Phylogenetic analysis of the nucleic acid sequences of HIV-1 gag and env genes has identified at least 5 subtypes, depending On the coding sequence considered (see Myers et al., 1993, Human Retrovirus and AIDS 1993, Los Alamos National Laboratory, Los Alamos, N. Mex., incorporated herein by reference). The most divergent HIV-1 have been identified in Africa. In particular, two divergent strains of HIV-1, designated ANT70 and MVP5180, were isolated from patients originating from Cameroon in West-Central Africa. Although the genomic organization of these isolates was similar to other HIV-1 subtypes, significant nucleotide sequence divergence was observed. The nucleic acid sequences of these isolates are available under accession numbers L20587 for ANT-70 and L20571 for MVP-5180. These new subtypes have been provisionally designated as subtype O.

SUMMARY OF THE INVENTION

The present invention provides improved oligonucleotide primers which enable the polymerase chain reaction (PCR) amplification of a region of the pol gene from all known subtypes of the human immunodeficiency virus type 1 (HIV-1), including subtype O. The present invention also provides improved oligonucleotide probes which enable the detection of HIV-1 nucleic acid by hybridization.

An important advantage of the primers of the present invention is that they enable amplification of all HIV-1 subtypes, including subtype O without the simultaneous amplification of non-target sequences. Thus, the primers enable an HIV-1 detection assay capable of detecting all subtypes of HIV-1 from samples originating from all regions of the world.

The oligonucleotide probes of the present invention hybridize to regions of the HIV-1 genome contained within the regions amplified using the primers of the present invention. The probes enable the specific detection of HIV-1 nucleic acid from all subtypes under a single set of hybridization conditions. When used to detect HIV-1 nucleic acid amplified with the probes of the invention, the specificity of the probes further increases the specificity of HIV-1 detection, thereby minimizing the probability of a false positive.

Another aspect of the invention relates to methods for amplifying a region of the pol gene from all HIV-1 subtypes which comprise carrying out a PCR using the primers of the invention.

Another aspect of the invention relates to methods for detecting HIV-1 which comprise amplifying a region of the HIV-1 pol gene by carrying out a PCR using the primers of the invention, and detecting the amplified DNA using the probes of the invention. The primers and probes of the present invention enable particularly simple and rapid methods for the specific detection of HIV-1 nucleic acid.

Another aspect of the invention relates to kits which contain the amplification primers of the invention. These kits can include additional reagents, such as the probes of the invention. The kits can also include one or more amplification reagents, e.g., polymerase, buffers, and nucleoside triphosphatase.

DETAILED DESCRIPTION OF THE INVENTION

To aid in understanding the invention, several terms are defined below.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1985, *Molecular Cloning—A Laboratory Manual*, Cold Spring Harbor Laboratory, Cold Spring Harbor, N.Y., incorporated herein by reference).

Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridization conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphatase and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template nucleic acid, but must be sufficiently complementary to hybridize with the template. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

As used herein, the "upstream" primer refers to the primer whose extension product is a subsequence of the coding strand. The "downstream" primer refers to the primer whose extension product is a subsequence of the complementary non-coding strand.

The term "probe", as used herein, refers to a oligonucleotide which forms a duplex structure with a sequence of a target nucleic acid due to complementary base pairing. Probes are used for detection or capture of the target nucleic acid. A probe is preferably a single-stranded oligodeoxyribonucleotide. The probe typically will consist of, or contain, a "hybridizing region" consisting preferably of from 10 to 50 nucleotides, more preferably from 15 to 35 nucleotides, corresponding to a region of the target sequence. "Corresponding" means at least substantially complementary to either the designated nucleic acid or its complement. A probe need not reflect the exact sequence of the target nucleic acid, but must be sufficiently complementary to hybridize with the target under the hybridization conditions chosen. A probe oligonucleotide can contain, or be bound to, additional features which allow for the detection or immobilization of the probe but do not significantly alter the hybridization characteristics of the hybridizing region. For example, probes may be labeled by the incorporation of radiolabeled nucleotides or by being bound to a separate detectable moiety.

As used herein, an oligonucleotide primer or probe is "specific" for a target sequence if the number of mismatches present between the oligonucleotide and the target sequence is less than the number of mismatches present between the oligonucleotide and non-target sequences. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. Thus, the use of target-specific probes under suitably stringent hybridization conditions enables the detection of a specific target sequence. Similarly, the use of target-specific primers under suitably stringent amplification conditions enables the specific amplification of those target sequences which contain the target primer binding sites.

The terms "target region" and "target nucleic acid" refers to a region of a nucleic acid which is to be amplified, detected, or otherwise analyzed. The sequence to which a primer or probe hybridizes can be referred to as a "target sequence".

The term "thermostable polymerase enzyme" refers to an enzyme that is relatively stable to heat and catalyzes the polymerization of nucleoside triphosphatase to form primer extension products that are complementary to one of the nucleic acid strands of the target sequence. The enzyme initiates synthesis at the 3' end of the primer and proceeds in the direction toward the 5' end of the template until synthesis terminates. A purified thermostable polymerase enzyme is described more fully in U.S. Pat. No. 4,889,818, incorporated herein by reference, and is commercially available from Perkin-Elmer, Norwalk, Conn.

The terms "amplification reaction mixture" and "polymerase chain reaction mixture" refer to a combination of reagents that is suitable for carrying out a polymerase chain reaction. The reaction mixture typically consists of oligonucleotide primers, nucleotide triphosphatase, and a DNA polymerase in a suitable buffer. Preferred amplification reaction mixtures are provided in the Examples.

The term "the complement of" a given nucleic acid refers specifically to the nucleic acid which is both the same length as, and exactly complementary to, the given nucleic acid. Thus, the complement of a nucleic acid refers to a single, uniquely defined sequence.

The term "subsequence" as used herein, refers to a sequence which is contained within a second sequence. As defined and used herein, subsequence is intended to include within its scope the full-length sequence. Thus, for example, probes which consist of a subsequence of SEQ ID NO: 5 include the probe which is SEQ ID NO: 5.

Conventional techniques of molecular biology and nucleic acid chemistry, which are within the skill of the art, are fully explained fully in the literature. See, for example, Sambrook et al., 1985, *Molecular Cloning—A Laboratory Manual*, Cold Spring Harbor Laboratory, Cold Spring Harbor, N.Y.; *Oligonucleotide Synthesis* (M. J. Gait, ed., 1984);

*Nucleic Acid Hybridization* (B. D. Hames and S. J. Higgins. eds., 1984); and a series, *Methods in Enzymology* (Academic Press, Inc.), all of which are incorporated herein by reference. All patents, patent applications, and publications mentioned herein, both supra and infra, are incorporated herein by reference.

HIV Amplification Primers

The high degree of sequence diversity among HIV-1 subtypes precludes amplification of HIV-1 nucleic acid using primers which are exactly complementary to all subtype sequences. Even relatively conserved regions still contain significant sequence variation. The present primers permit amplification of all the HIV-1 subtypes despite the sequence variability present within the primer hybridizing regions.

The primers of the present invention hybridize to relatively conserved regions within the pol gene, which minimizes the variability which must be accommodated in the amplification. The primers of the invention contain between 1 and 5 mismatches with each of the HIV-1 subtypes. As described in the Examples, amplifications are carried out under conditions which permit up to 5 base pair mismatches and, therefore, enable amplification of all HIV-1 subtypes. Thus, the primers of the present invention enable the specific amplification of pol gene nucleic acid from the known HIV-1 subtypes.

In general, a mismatch at the Y end of a primer, which is the primer extension site, has a greater affect on primer extension than a base-pair mismatch occurring away from the 3' end. However, the destabilizing affect of a base-pair mismatch depends on the bases involved, with a mismatch involving a thymidine being the least destabilizing (see Kwok et al., 1990, *Nuc. Acids Reds.* 18:999–1005, incorporated herein by reference). To minimize the destabilizing affect of a mismatch at the 3' end of the primers, each of the primers contains a thymidine at the 3' end. Thus, the present primers are likely to amplify new HIV-1 isolates which differ, by chance, at a critical 3' terminal base of a primer.

The affect of a destabilizing base-pair mismatch also depends on the length of the primer. Longer primers are less affected by a single mismatch. Using the present primers, which are 32 to 33 bases in length, the amplification reaction is able to accommodate the minor sequence variability expected in new HIV-1 isolates, while not amplifying less homologous sequences from other organisms.

The sequences of the primers are provided in Table 1, shown in the 5' to 3' orientation.

The hybridization specificity of the primers is a critical property of the primers which enables the amplification of the known HIV-1 subtypes without the simultaneous amplification of homologous non-target sequences from other viruses or from human genomic DNA. Because the hybridization specificity of a primer depends on the exact length and base composition of the hybridizing region, minor modifications in sequence of the primer hybridizing region can adversely affect the utility of the primers. In essence, the primer hybridizing regions must consist of the sequences provided in Table 1. However, one of skill in the art will realize that some specific minor modifications, such as single base deletion or addition at the 5' end, may be possible without significantly affecting the hybridization specificity and utility. Such modifications typically will require optimization of the hybridization conditions in a routine manner. Primers which have been altered without appreciably changing the hybridization specificity are considered to be equivalent.

Amplification

The polymerase chain reaction (PCR) amplification process is well known in the art and described in U.S. Pat. Nos. 4,683,195; 4,683,202; and 4,965,188, each incorporated herein by reference, and in Saiki et al., 1988, *Science* 239:487; Scharf et al., 1988, *Hum. Immunol.* 22:61; and Scharf et al., 1989, *Proc. Natl. Acad. Sci. USA* 86:6215, each incorporated herein by reference. Commercial vendors, such as Perkin Elmer, Norwalk, Conn., market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

Various suitable sample preparation methods suitable for PCR have been described in the literature. The particular method used is not a critical part of the present invention. One of skill in the art can optimize reaction conditions for use with the known sample preparation methods. Preferred

TABLE 1

HIV-1 Amplification Primers

| Primer | Seq. ID No. | Sequence |
|---|---|---|
| RAR1032 | 1 | 5'-TGA GAC ACC AGG AAT TAG ATA TCA GTA CAA TGT |
| RAR1033 | 2 | 5'-CTA AAT CAG ATC CTA CAT ATA AGT CAT CCA TGT |
| RAR1035 | 3 | 5'-AGC AGT ACA AAT GGC AGT GTT CAT TCA CAA TT |
| RAR1036 | 4 | 5'-TTT ATC TTG TAT TAC TAC TGC CCC TTC ACC TTT |

Upstream primer RAR1032 (SEQ ID NO: 1) and downstream primer RAR1033 (SEQ ID NO: 2) amplify a 170 base pair product corresponding to nucleotide positions 2959 to 3128 of the sequence of HIV-1 reference strain HXB2 (GenBank accession no. K03455). Upstream primer RAR1035 (SEQ ID NO: 3) and downstream primer RAR1036 (SEQ ID NO: 4) amplify a 241 base pair product corresponding to nucleotide positions 4750 to 4990.

sample preparation methods for use in the detection of HIV-1 proviral DNA are described in Casareale et al., 1992, in PCR Methods and Applications 2:149–153, incorporated herein by reference.

The methods of the present invention may be used to detect either HIV-1 proviral DNA or HIV-1 RNA. The amplification of RNA using a reverse transcription/polymerase chain reaction (RT-PCR) is well known in the art and described in U.S. Pat. Nos. 5,322,770 and 5,310,652, Myers and Gelfand, 1991, *Biochemistry* 30(31):7661–7666, Young et al., 1993, *J. Clin. Microbiol.* 31(4):882–886, and Mulder et al., 1994, *J. Clin. Microbiol.* 32(2):292–300, each incorporated herein by reference.

Due to the enormous amplification possible with the PCR process, small levels of DNA carryover from samples with high DNA levels, positive control templates, or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Kwok and Higuchi, 1989, *Nature*, 339:237–238 and Kwok, and Orrego, in: Innis et at. eds., 1990 *PCR Protocols: A Guide to Methods and Applications*. Academic Press, Inc., San Diego, Calif., which are incorporated herein by reference.

Enzymatic methods to reduce the problem of contamination of a PCR by the amplified nucleic acid from previous reactions are described in PCT patent publication Ser. No. US 91/05210 and U.S. Pat. No. 5,035,996, both incorporated herein by reference. The methods allow the enzymatic degradation of any amplified DNA from previous reactions. PCR amplifications are carried out in the presence of dUTP instead of dTTP. The resulting double-stranded amplification product which incorporates uracil is subject to degradation by uracil-N-glycosylase (UNG), whereas normal thymine-containing DNA is not degraded by UNG. Amplification reaction mixture are treated with UNG before amplification to degrade all uracil containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-inactivated environment and are not degraded.

Amplification reaction mixtures are typically assembled at room temperature, well below the temperature needed to insure primer hybridization specificity. Non-specific amplification may result because at room temperature the primers may bind non-specifically to other, only partially complementary nucleic acid sequences, and initiate the synthesis of undesired nucleic acid sequences. These newly synthesized, undesired sequences can compete with the desired target sequence during the amplification reaction and can significantly decrease the amplification efficiency of the desired sequence. Non-specific amplification can be reduced using a "hot-start" protocol wherein one or more reagents are withheld from the reaction mixture until the temperature is raised sufficiently to provide the necessary hybridization specificity.

Preferred methods of reducing non-specific amplification are described in U.S. Pat. No. 5,418,149, which is incorporated herein by reference. The methods described therein reduce non-specific amplification by degrading any newly synthesized nucleic acid synthesized after the reaction mixture is assembled but prior to the start of the amplification reaction. By degrading any newly synthesized nucleic acid, no amplifiable nucleic acid target sequences resulting from primers hybridized to unintended sequences are present when the high temperature amplification reaction is carried out. The degradation of newly-synthesized nucleic acid is achieved by incorporating into the reaction mixture dUTP and UNG, and incubating the reaction mixture at 45°–60° C. prior to carrying out the amplification reaction.

Analysis of Amplified Product

Following amplification, the presence of HIV-1 nucleic acid is determined by detecting amplified product. Methods for detecting PCR amplified nucleic acids are well known in the art. For example, the presence and quantity of amplified product can be assayed using gel electrophoresis. The detection of amplification product by gel electrophoresis is well known in the art (see, for example, Sambrook et al., 1989, supra).

Detection of the amplified product is preferably carried out by hybridization with an oligonucleotide probe. Probes of the invention used for detecting the DNA amplified using the primers of Table 1 are shown in Table 2, below. The complement of each of the probes is equally useful in the methods described herein. Preferred hybridization conditions are described in the Examples.

TABLE 2

HIV-1 Probes

| Primer | Seq. ID No. | Sequence |
|---|---|---|
| RAR1034 | 5 | 5'-CCA CAA GGA TGG AAA GGA TCA CCA GCT ATA TTC CA |
| RAR1037 | 6 | 5'-ACA GGG ACA GCA GAG ATC CTA TTT GGA AAG GAC CA |
| RAR1034T | 7 | 5'-GGA TGG AAA GGA TCA CCA GCT ATA TTC CA |
| RAR1037T | 8 | 5'-ACA GCA GAG ATC CTA TTT GGA AAG GAC CA |

RAR1034 (SEQ ID NO:5) hybridizes to the HIV-1 genome at positions 2996 to 3030 and is used to detect DNA amplified using primers RAR1032 (SEQ ID NO: 1) and RAR1033 (SEQ ID NO: 2). RAR1037 (SEQ ID NO: 6) hybridizes to the HIV-1 genome at positions 4908 to 4942 and is used to detect DNA amplified using primers RAR1035 (SEQ ID NO: 3) and RAR1036 (SEQ ID NO: 4).

RAR1034T (SEQ ID NO: 7) differs from RAR1034 (SEQ ID NO: 5) in that the 5' terminal 6 bases are deleted. Although both the full-length and truncated probes have been demonstrated to function well in the 5'-nuclease assay described below and in Example 6, RAR1034T (SEQ ID NO: 7) is preferred. Similarly, RAR1037T (SEQ ID NO: 8), which differs from RAR1037 (SEQ ID NO: 6) in that the 5' terminal 6 bases are deleted, may be preferred for use in the 5'-nuclease assay described below and in Example 6. Thus, the full-length probes, RAR1034 (SEQ ID NO: 5) and RAR1037 (SEQ ID NO: 6), are preferred for use in the microwell plate assay described in Examples 1–3, and the probes which consist of the full-length sequence truncated at the 5' end by 6 bases, RAR1034T (SEQ ID NO: 7) and RAR1037T (SEQ ID NO: 8), are preferred for use in the 5' nuclease assay described in Example 6. In addition, probes which consist of the full-length sequence truncated at the 5' end by between 1 and 5 bases also are suitable in the methods of the present invention. Consequently, the probes of the present invention consist of a subsequence of a full-length probe, RAR1034 (SEQ ID NO: 5) or RAR1037 (SEQ ID NO: 6), wherein the subsequence comprises bases 7–35 of the full-length sequence, or the complement thereof. The numbering of the probes is relative to the 5' end.

As with the primers, the probes of the invention contain a small number of mismatches (between 1 and 5, and between 1 and 4, respectively) with each of the HIV-1 subtypes. The hybridization conditions described in the Examples allow hybridization of the probes to any of the HIV-1 subtypes, without allowing hybridization to less homologous sequences from other organisms. Thus, the probes of the invention enable the specific detection of HIV-1 nucleic acid.

Suitable assay formats for detecting hybrids formed between probes and target nucleic acid sequences in a sample are known in the art (Sambrook et al., 1985, supra). Examples include the dot-blot and reverse dot-blot assay formats.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

An alternate format is a "reverse" dot-blot format, in which the amplified target DNA is labeled and the probes are immobilized on a solid support, such as a nylon membrane (see Saiki et al., 1989, *Proc. Natl. Acad. Sci. USA* 86:6230, and PCT Patent Publication No. 89/11548, both incorporated herein by reference). The target DNA is typically labeled during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the filter is then monitored for the presence of bound target DNA.

Alternatively, the reverse dot-blot assay can be carried out using a solid support having a plurality of probe hybridization sites or wells. For example, a microwell plate is particularly useful in large scale clinical applications of the present methods. Probes can be immobilized to a microwell plate either by passive binding or through a protein intermediate, such as bovine serum albumin (BSA), which adheres to microwell plates. Reverse dot-blot methods carried out in a microwell plate are described in copending U.S. Ser. No. 141,355, U.S. Pat. No. 5,232,829, and Loeffelholz et al, 1992, *J. Clin. Microbiol.* 30(11):2847–2851, each incorporated herein by reference, and in Mulder et al., 1994, supra, and Jackson et al., 1991, supra.

In an alternative method of immobilizing hybridization duplexes for detection, BSA-conjugated probes are bound to magnetic microparticles. The bound probes are hybridized in solution to labeled amplification product. Following hybridization, probe-target duplexes are removed from the solution magnetically, and the magnetically immobilized hybridization duplexes are then detected as in the methods described above.

Another suitable assay method, referred to as a 5'-nuclease assay, is described in U.S. Pat. No. 5,210,015, incorporated herein by reference, in which the labeled detection probes are added during the PCR amplification process. The probes are modified so as to prevent the probes from acting as primers for DNA synthesis. Any probe which hybridizes to target DNA during each synthesis step, i.e., during primer extension, is degraded by the 5' to 3' exonuclease activity of the DNA polymerase, e.g., Taq DNA polymerase. The degradation product from the probe is then detected. Thus, the presence of probe breakdown product indicates both that hybridization between probe and target DNA occurred and that the amplification reaction occurred. Probes of Table 2 which have been modified to function in the methods of the U.S. Pat. No. 5,210,015 are within the scope of the present invention. U.S. Pat. No. 5,491,063 and copending U.S. Ser. No. 08/347,657, filed Nov. 23, 1994, now allowed, both incorporated herein by reference, describe improved methods for detecting the degradation of probe which occurs concomitant with amplification.

The assay formats described above typically utilize labeled oligonucleotides to facilitate detection of the hybrid duplexes. Oligonucleotides can be labeled by incorporating a label detectable by spectroscopic, photochemical, biochemical, immunochemical, or chemical means. Useful labels include $^{32}P$, fluorescent dyes, electron-dense reagents, enzymes (as commonly used in ELISAS), biotin, or haptens and proteins for which antisera or monoclonal antibodies are available. Labeled oligonucleotides of the invention can be synthesized and labeled using the techniques described above for synthesizing oligonucleotides.

In a preferred embodiment of the invention, a reverse dot-blot assay is carried out using microwell plates, and the primers are labeled with biotin, as described in Levenson and Chang, 1989, in *PCR Protocols: A Guide to Methods and Applications*, (Innis et al., eds., Academic Press. San Diego) pages 99–112, incorporated herein by reference. The probes are conjugated with BSA (see Tung et al., 1991, *Bioconjugate Chem.* 2:464–465, incorporated herein by reference) and immobilized on a microwell plate. Following amplification using the labeled primers and hybridization with the immobilized probes, the amplified nucleic acid is detected by first binding the biotin to avidin-horseradish peroxidase (A-HRP) or streptavidin-horseradish peroxidase (SAHRP), which is then detected by carrying out a reaction in which the HRP catalyzes a color change of a chromogen (see Saiki et al., 1989, supra).

An alternative method for detecting the amplification of HIV-1 nucleic acid by monitoring the increase in the total amount of double-stranded DNA in the reaction mixture is described in Higuchi et al., 1992, *Bio/Technology* 10:413–417; Higuchi et al., 1993, *Bio/Technology* 11:1026–1030; and European Patent Publication Nos. 487, 218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence. The primers of the present invention are particularly useful because they enable amplification with unusually low levels of background non-specific amplification products.

The present invention also relates to kits, multicontainer units comprising useful components for practicing the present method. A useful kit can contain primers for the PCR amplification of HIV-1 nucleic acid. A kit can also contain means for detecting amplified HIV-1 nucleic acid, such as oligonucleotide probes. In some cases, the probes are fixed to an appropriate support membrane. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Amplification and Detection of H/V-1 DNA

The following methods were used to amplify and detect HIV-1 proviral DNA from clinical samples as described in the subsequent examples.

Sample Preparation

In a first method, peripheral blood monocytes were isolated by the standard Ficoll-Hypaque density gradient method described in Boyum, 1968, *Scan. J Clin. Lab. Invest.* 21 (Suppl. 97):77, and Fotino et al., 1971, *Ann. Clin. Lab. Sci.* 1:131–133, both incorporated herein by reference.

In a second method, white blood cells were isolated from 0.5 ml peripheral blood by direct red blood cell lysis as described Casareale et al., 1992, *PCR Methods and Applications* 2;149–153, incorporated herein by reference. Following isolation of the cells, the DNA was extracted as described in Casareale et al., 1992, supra, and in Butcher and Spadoro, 1992, *Clin. Immunol. Newsletter* 12:73–76, incorporated herein by reference.

Amplification

Amplifications using primers RAR1032 (SEQ ID NO: 1) and RAR1033 (SEQ ID NO: 2) were carried out in 100 μl reactions volumes (50 μl from the sample). Each reaction contained the following reagents:

10 mM Tris-HCl (pH 8.4), 50 mM KCl,

200 μM each dATP, dCTP, dGTP, and dUTP, 25 pmoles of each biotinylated primer, 3.0 mM $MgCl_2$, 10% Glycerol.

2.0 units of Taq DNA polymerase*, and 2.0 units of UNG*.

*manufactured and developed by Hoffmann-La Roche and marketed by Perkin Elmer, Norwalk, Conn.

Amplifications using primers RAR1035 (SEQ ID NO: 3) and RAR1036 (SEQ ID NO: 4) were carried out under essentially identical conditions, except that the reactions contained 2.0 mM $MgCl_2$.

Amplifications were carried out in a TC9600 DNA thermal cycler (Perkin Elmer, Norwalk, Conn.) using the following temperature profile:

| | |
|---|---|
| Pre-reaction incubation | 50° C. for 2 minutes; |
| Initial cycle: | denature at 94° C. for 30 seconds, anneal at 50° C. for 30 seconds, and extend at 72° C. for 30 seconds; |

In cycles 2–4, the annealing temperature was increased in 2° C. increments (to 58° C.).

| | |
|---|---|
| 35 cycles: | denature at 90° C. for 30 seconds, anneal at 60° C. for 30 seconds, and extend at 72° C. for 30 seconds; |

Following the temperature cycling, the reaction mixture preferably is analyzed immediately. The reaction can be held at 72° C. for a short time before analysis. Alternatively, the PCR tubes can be stored at −20° C. and briefly warmed to 25° C. to 30° C. prior to opening.

Detection of Amplified Product

A. Gel Electrophoresis The presence of amplified product was detected by gel electrophoresis as follows. Reaction products were fractionated using an agarose gel (100 ml of 3% NuSieve and 0.5% SeaChem) and 1X TE (0.089M Tris, 0.089 M boric acid, 0.0025M disodium EDTA) running buffer are used. Electrophoresis was carried out at 100 volts for approximately 1 hour. Ethidium bromide (0.5 μg/ml) was added following electrophoresis to stain any DNA present. The gel was destained briefly in water and the ethidium bromide-stained bands of DNA were visualized using UV irradiation.

B. Probe Hybridization

Amplified products were assayed in a reverse dot-blot format using probes immobilized on microwell plates. In this detection format, the probes were immobilized to a well of a microwell plate and the denatured amplified target DNA was hybridized to the bound probes. The amplifications described above were carried out using biotinylated primers to allow detection of amplified DNA that hybridizes to the bound probes.

Amplified DNA was denatured by the addition of an equal volume of denaturation solution (0.4M NaOH; 80 mM EDTA and 0.005% Thymol blue) to each PCR tube. A new pipette tip was used for each tube.

Probes were immobilized on microwell plates through a bovine serum albumen (BSA) intermediate. Probes conjugated to BSA were allowed to adsorb to the plastic surface of the individual wells of a 96 well plate (Corning, Corning, N.Y.). Probes were immobilized on the microwell plate at a concentration of 15 ng/well.

Alternatively, probes can be immobilized passively on the plastic surface of a microwell plate as follows. One hundred μl of a solution of 1M $CH_3COONH_4$ containing probe at a concentration of 0.125 ng/μl are added into each well of a microwell plate. The plate is incubated at 37° C. for 10 to 20 hours (overnight) and then rinsed with PBS/EDTA (PBS is 2.68 mM KCl, 137 mM NaCl, 1.47 mM $KH_2PO_4$, and 8.03 mM $Na_2HPO_4$).

The appropriate number of eight well microwell plate strips (minimally 2 strips) were removed and set into the microwell plate frame. One hundred μl of hybridization/neutralization buffer (2.5M NaSCN, 80 mM $NaH_2PO_4$, 10 mM $NaH_2PO_4$, and 0.125% Tween 20; pH 5.0±0.2) were pipetted into each well of the microwell plate. Using plugged tips with a multi-channel pipetter, 25 μl of the denatured amplification reaction from each PCR tube in the tray were pipetted to the corresponding well position in the microwell plate. The plate was covered with the microwell plate lid and gently tapped on the side approximately 10 to 15 times until the color changes from blue to light yellow.

The plate was incubated for 60 minutes at 37° C. to allow hybridization. Following incubation, the plate was washed five times with a 1X wash solution. A 10X concentrate of wash solution contains 9.94 g/l sodium phosphate dibasic, 4.41 g/l sodium phosphate (monobasic), 3.722 g/l EDTA, 87.66 grams per liter sodium chloride, 13.7 g/l Tween 20, and 10 g/l Pro Clin 300 (Rohm and Haas, Philadelphia, Pa.). The pH of the solution is adjusted with phosphoric acid (pH 6.5–7.1 is preferred). Washing of the plate may be performed manually or with an automated microwell plate washer programmed accordingly.

For manual washing the contents of the plate are emptied and tapped dry. Each well is filled with wash solution (400–450 μl), the plate is allowed to soak for 30 seconds, and the plate is again emptied and tapped dry. This wash process is repeated four additional times.

For an automated microplate washer, the following procedure is used. The contents of the wells are aspirated. The washer is programmed to add 350–450 μl of wash solution to each well in the plate being tested, soak for 30 seconds, and aspirate. The steps are repeated four additional times. The plate is then tapped dry.

One hundred μl of avidin-HRP conjugate (available from multiple sources, e.g., Fluka Chemical Corp., Ronkonkoma, N.Y., and Sigma Chemical Co., St. Louis, Mo.) were added to each well in the plate. The plate was covered and incubated 15 minutes at 37° C. and again washed as described above. One hundred μl of a chromogen solution containing tetramethylbenzadine (available from multiple sources, e.g., Fluka Chemical Corp., Ronkonkoma, N.Y., and Sigma Chemical Co., St. Louis, Mo.) and $H_2O_2$ were added to each well of the plate. The plate was then covered and incubated in the dark for 10 minutes at room temperature (20° C. to 25° C.) to allow the color to develop. Finally, 100 μl of Stop Reagent (5% $H_2SO_4$) was added to each well. The absorbance of each well of 450 nM was read within one hour of adding the Stop Reagent.

EXAMPLE 2

Detection of HIV DNA in Clinical Samples

In this example, 91 samples obtained from seropositive patients from the Ivory Coast, Africa, were assayed for the presence of HIV DNA. For comparison, amplifications and detection also were carried out using primers and probes described in the literature.

Peripheral blood monocytes were isolated by the Ficoll-Hypaque density gradient method described in Example 1. Amplification and detection were carried out as described in Example 1 using primer pair RAR1032 (SEQ ID NO: 1) and RAR1033 (SEQ ID NO: 2) and probe RAR1034 (SEQ ID NO: 5), and using primer pair RAR1035 (SEQ ID NO: 3) and RAR1036 (SEQ ID NO: 4) and probe RAR1037 (SEQ ID NO: 6).

For comparison, separate amplification/detection assays were carried out using 2 additional primer/probe sets which have been described in the literature. Primers SK462 and SK431, and probe SK102, are described in Jackson et al. supra. Primers SK38 and SK39, and probe SK19, are described in Kellogg and Kwok, 1990, supra. Amplifications using primer pairs SK462/SK431 and SK38/SK39 were carried out essentially as described in Example 1, but using the following conditions.

Each reaction contained the following reagents:

10 mM Tris-HCl (pH 8.4), 50 mM KCl,

200 μM each dATP, dCTP, dGTP, and dUTP, 25 pmoles of each biotinylated primer, 3.75 mM $MgCl_2$, 10% Glycerol, 2.0 units of Taq DNA polymerase*, and 2.0 units of UNG*.

*manufactured and developed by Hoffmann-La Roche and marketed by Perkin Elmer, Norwalk, Conn.

Amplifications were carried out in a TC9600 DNA thermal cycler (Perkin Elmer, Norwalk, Conn.) using the following temperature profile:

| Pre-reaction incubation: | 50° C. for 2 minutes |
| --- | --- |
| 5 cycles: | denature at 95° C. for 10 seconds, anneal at 55° C. for 10 seconds, and extend at 72° C. for 10 seconds; |
| 30 cycles: | denature at 90° C. for 10 seconds, anneal at 60° C. for 10 seconds, and extend at 72° C. for 10 seconds; |
| Hold: | 72° C. |

Following amplification, the presence of amplified DNA was detected essentially as described in Example 1 using BSA-conjugated probes SK102 and SK19 immobilized on microwell plates.

Results comparing the primer and probe sets are shown in the table, below, as the number of samples from which HIV-1 was detected out of the total number of each subtype assayed, and the corresponding per cent detected.

| Primer Pair | Probe | No. Detected | % Detected |
| --- | --- | --- | --- |
| RAR1032/RAR1033 | RAR1034 | 90/91 | 98.9% |
| RAR1035/RAR1036 | RAR1037 | 90/91 | 98.9% |
| SK462/SK431 | SK102 | 64/91 | 70.3% |
| SK38/SK39 | SK19 | 86/91 | 94.5% |

Both of the assays of the present invention were able to detect HIV-1 from almost all of the samples tested. In contrast, both the assay using primer pair SK462 and SK431 and probe SK102, and the assay using primer pair SK38 and SK39 and probe SK19 failed to detect HIV-1 DNA from a greater number of the samples. The single sample not detectable using the primers and probes of the present invention also was not detected using the SK primers and probes. The reason that HIV-1 was not detectable from this sample may be caused by poor sample quality or an unusually low virus titer.

EXAMPLE 3

Detection of HIV in Clinical Samples

In this example, 41 samples were assayed for the presence of HIV-1 DNA. The samples were obtained from seropositive patients from the Ivory Coast, Africa.

White blood cells were isolated from 0.5 ml peripheral blood by the direct red blood cell lysis method described in Example 1. Amplification reactions and detection assays were carried out as described in Examples 1 and 2. Results are shown in the table, below, as the number of samples from which HIV-1 was detected out of the total number of each subtype assayed, and the corresponding per cent detected.

| Primer Pair | Probe | No. Detected | % Detected |
| --- | --- | --- | --- |
| RAR1032/RAR1033 | RAR1034 | 40/41 | 97.6% |
| RAR1035/RAR1036 | RAR1037 | 40/41 | 97.6% |
| SK462/SK431 | SK102 | 36/41 | 87.8% |
| SK38/SK39 | SK19 | 40/41 | 97.6% |

EXAMPLE 4

Amplification and Detection of Known HIV-1 Subtypes

A total of 18 DNA extracts from known HIV-1 subtypes were assayed essentially as described in Examples 1–3, above. DNA from subtypes A–F were obtained from clinical samples. DNA from subtype O was obtained from an infected cell line. All DNA samples were extracted with a proteinase K solution essentially as described in Casareale et at., 1992, supra.

The results are shown in the table, below, as the number of samples of each subtype from which HIV-1 was detected out of the total number of each subtype assayed.

|             | HIV-1 Types |     |     |     |     |     |     |       |
| ----------- | --- | --- | --- | --- | --- | --- | --- | ----- |
| Primer Pair | A   | B   | C   | D   | E   | F   | O   | Total |
| RAR1032/RAR1033 | 1/1 | 3/3 | 2/2 | 2/2 | 8/8 | 1/1 | 1/1 | 18/18 |
| SK462/SK431 | 1/1 | 3/3 | 2/2 | 2/2 | 7/8 | 1/1 | 0/1 | 16/18 |
| SK38/SK39   | 1/1 | 3/3 | 2/2 | 1/2 | 6/8 | 0/1 | 0/1 | 13/18 |

HIV-1 was detected from all 18 HIV-1 samples assayed using primer pair RAR1032 (SEQ ID NO: 1) and RAR1033 (SEQ ID NO: 2) and probe RAR1034 (SEQ ID NO: 5). In contrast, both the assay using primer pair SK462 and SK431 and probe SK102, and the assay using primer pair SK38 and SK39 and probe SK19 failed to detect HIV-1 subtype O DNA. Furthermore, the assay using primer pair SK462 and SK431 and probe SK102 failed to detect HIV-1 subtype E from one of the samples. The assay using primer pair SK38 and SK39 and probe SK19 failed to detect HIV-1 subtype E from 2 of the samples and failed to detect HIV-1 subtype F.

EXAMPLE 5

Detection of HIV-1 RNA

HIV-1 RNA can be amplified using the GeneAmp® EZ rTth RNA PCR kit (Perkin Elmer, Norwalk, Conn.). Sample preparation is carried out as described in Mulder et at., 1994, supra. Detection of the amplified product is carried out as described in Example 1.

EXAMPLE 6

5'-Exonuclease Assay

This example describes the use of the primers and probes of the present invention in the methods described in U.S. Pat. No. 5,210,015. A labeled probe which was modified so as to prevent the probe from acting as a primer for DNA synthesis was added during the PCR amplification process. Any probe which hybridized to the HIV-1 DNA was degraded by the 5' to 3' exonuclease activity of the rTth DNA polymerase during amplification. The detection of degraded probe indicated the presence of HIV-1 DNA.

The probe used was the complement of RAR1034T (SEQ ID NO: 7) which had been synthesized with a FAM label (Perkin Elmer, Applied Biosystems Division, Foster City, Calif.) bound at the 5' end and a 3'-PO4 instead of a 3'-OH to block any extension by the DNA polymerase.

Samples containing HIV-1 DNA were prepared as described above. Reactions were carried out in 100 μl volumes containing the following reagents:

50 mM Tricine (pH 8.2), 110 mM KOAc,

300 μM each dATP, dCTP; and dGTP,

500 μM each dTTP and dUTP, 50 pmoles of each primer, 100 pmoles probe 2.4 mM $Mn(AOc)_2$, 12% Glycerol, 2 units UNG*, and 20 units of rTth DNA polymerase*.

*manufactured and developed by Hoffmann-La Roche and marketed by Perkin Elmer, Norwalk, Conn.

The detection of degraded probe can be carried out using the methods described in the U.S. Pat. No. 5,210,015 and in U.S. Pat. No. 5,491,063 and copending U.S. Ser. No. 08/347, 657 now allowed.

---

I claim:

1. A pair of oligonucleotide primers consisting of RAR1032 (SEQ ID NO: 1) and RAR1033 (SEQ ID NO: 2).

2. A pair of oligonucleotide primers consisting of RAR1035 (SEQ ID NO: 3), and RAR1036 (SEQ ID NO: 4).

3. An oligonucleotide probe for the detection of human immunodeficiency virus nucleic acid, wherein said oligonucleotide probe consists of a subsequence of RAR1037 (SEQ ID NO: 6) comprising bases 7 through 35, or the complement thereof.

4. An oligonucleotide probe of claim 3 which is selected from the group consisting of RAR1037 (SEQ ID NO: 6), RAR1037T (SEQ ID NO: 8), and the complements thereof.

5. A kit for detecting human immunodeficiency virus type 1 (HIV-1) nucleic acid, wherein said kit comprises a pair of oligonucleotide primers of claim 1.

6. A kit for detecting human immunodeficiency virus type 1 (HIV-1) nucleic acid, wherein said kit comprises a pair of oligonucleotide primers of claim 2.

7. A kit of claim 5, further comprising an oligonucleotide probe consisting of a subsequence of RAR1034 (SEQ ID NO: 5) comprising bases 7 through 35, or the complement thereof.

8. A kit of claim 6, further comprising an oligonucleotide probe consisting of a subsequence of RAR1037 (SEQ ID NO: 6) comprising bases 7 through 35, or the complement thereof.

9. A method for detecting human immunodeficiency virus type 1 (HIV-1) nucleic acid, wherein said method comprises:

(a) carrying out a polymerase chain reaction using a pair of oligonucleotide primers of claim 1; and (b) detecting amplified HIV-1 nucleic acid.

10. A method of claim 9, wherein step (b) is carried out using an oligonucleotide probe consisting of a subsequence of RAR1034 (SEQ ID NO: 5) comprising bases 7 through 35, or the complement thereof.

11. A method for detecting human immunodeficiency virus type 1 (HIV-1) nucleic acid, wherein said method comprises:

(a) carrying out a polymerase chain reaction using a pair of oligonucleotide primers of claim 2; and (b) detecting amplified HIV-1 nucleic acid.

12. A method of claim 11, wherein step (b) is carried out using an oligonucleotide probe consisting of a subsequence of RAR1037 (SEQ ID NO: 6) comprising bases 7 through 35, or the complement thereof.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TGAGACACCA GGAATTAGAT ATCAGTACAA TGT    33

( 2 ) INFORMATION FOR SEQ ID NO:2:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

```
CTAAATCAGA TCCTACATAT AAGTCATCCA TGT                    33
```

( 2 ) INFORMATION FOR SEQ ID NO:3:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

```
AGCAGTACAA ATGGCAGTGT TCATTCACAA TT                     32
```

( 2 ) INFORMATION FOR SEQ ID NO:4:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

```
TTTATCTTGT ATTACTACTG CCCCTTCACC TTT                    33
```

( 2 ) INFORMATION FOR SEQ ID NO:5:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

```
CCACAAGGAT GGAAAGGATC ACCAGCTATA TTCCA                  35
```

( 2 ) INFORMATION FOR SEQ ID NO:6:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

```
ACAGGGACAG CAGAGATCCT ATTTGGAAAG GACCA                  35
```

( 2 ) INFORMATION FOR SEQ ID NO:7:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear (ii) MOLECULE TYPE: DNA (genomic)

(xi) SEQUENCE DESCRIPTION: SEQ ID NO:7:

GGATGGAAAG GATCACCAGC TATATTCCA 29

(2) INFORMATION FOR SEQ ID NO:8:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:8:

ACAGCAGAGA TCCTATTTGG AAAGGACCA 29